US00PP12828P2

(12) United States Plant Patent
Plattner

(10) Patent No.: US PP12,828 P2
(45) Date of Patent: Aug. 6, 2002

(54) FIG TREE NAMED 'VIOLETTA'

(75) Inventor: Anton Plattner, Aldersbach (DE)

(73) Assignee: Anton Plattner Baumschule, Aldersbach (DE)

( * ) Notice: Subject to any disclaimer, the term of this patent is extended or adjusted under 35 U.S.C. 154(b) by 0 days.

(21) Appl. No.: 09/519,864

(22) Filed: Mar. 6, 2000

(51) Int. Cl.[7] ..... A01H 5/00
(52) U.S. Cl. ..... Plt./156

(58) Field of Search ..... Plt./156

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Fig tree named 'Violetta' characterized by its upright plant habit; rapid growth rate and early fruit production; early ripening; high fruit yield; large and very sweet-tasting fruit with edible sweet, not bitter, skin; and tolerance to low temperatures; typically tolerant to temperatures about −20° C.

2 Drawing Sheets

BACKGROUND OF THE INVENTION

The present Invention relates to a new and distinct cultivar of Fig tree, botanically known as *Ficus carica*, and hereinafter referred to by the cultivar name Violetta.

The new Fig tree is a naturally-occurring whole plant mutation of an unidentified selection of *Ficus carica*. The new Fig tree was discovered by the Inventor in Haag, Germany in 1983. The new Fig tree was selected based on its extraordinary low temperature tolerance compared to the parent and commercial cultivars of *Ficus carica*.

Asexual reproduction of the new cultivar by vegetative cuttings taken in Haag, Germany, has shown that the unique features of this new Fig tree are stable and reproduced true to type in successive generations of asexual reproduction.

SUMMARY OF THE INVENTION

The following traits have been repeatedly observed and are determined to be the unique characteristics of 'Violetta'. These characteristics in combination distinguish 'Violetta' as a new and distinct cultivar.

1. Upright plant habit.
2. Fast growth rate and early fruit production.
3. Early ripening; typically late July to early August in Central Europe.
4. High fruit yield.
5. Large and very sweet-tasting fruit with edible sweet, not bitter, skin.
6. Tolerance to low temperatures; typically tolerant to temperatures about −20° C.

Plants of the new Fig tree can be compared to plants of the nonpatented *Ficus carica* cultivar Pfalzer Feige. In side-by-side comparisons conducted by the Inventor in Haag, Germany, plants of the new Fig tree developed fruit on younger plants and also produced more fruit per plant than plants of the cultivar Pfalzer Feige.

Plants of the new Fig tree can also be compared to plants of the nonpatented *Ficus carica* cultivar Italienische Feige. In side-by-side comparisons conducted by the Inventor in Haag, Germany, plants of the new Fig tree developed fruit on younger plants, produced more fruit per plant, and were more winter hardy than plants of the cultivar Pfalzer Feige.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Fig tree.

The photograph on the first sheet comprises a side perspective view of a typical five year old plant of 'Violetta' growing on a trellis.

The photograph on the second sheet comprises a side perspective view of typical young plants of 'Violetta' grown in containers; the plant on the right was about two years old and the plant on the left was about one year old.

DETAILED BOTANICAL DESCRIPTION

Plants of the cultivar Violetta have not been observed under all possible environmental conditions. The phenotype may vary somewhat with variations in environment such as temperature and light intensity, without, however, any variance in genotype. The following observations, measurements and comparisons describe plants grown in Haag, Germany, in a polyethylene-covered greenhouse with day temperatures ranging from 15 to 30° C. and night temperatures ranging from 10 to 20° C. Plants used for the description ranged from one to about five years old.

In the following description, color references are made to The Royal Horticultural Society Colour Chart except where general terms of ordinary dictionary significance are used.

Botanical classification: *Ficus carica* cultivar Violetta.
Parentage: Naturally-occurring whole plant mutation of an unidentified selection of *Ficus carica*.
Propagation:
- *Type cutting.*—Vegetative cuttings.
- *Time to initiate roots.*—Summer: About 20 to 30 days. Winter: About 30 to 40 days.
- *Time to produce a rooted cutting or liner.*—Summer: About 40 days. Winter: About 56 days.
- *Rooting habit.*—Fleshy; not freely branching.

Plant description:

*General appearance/growth habit.*—Perennial, deciduous, fruiting shrub; upright and rounded. Plants are typically produced in 3 to 30-liter containers.

*Growth rate.*—About 50 to 100 cm per year; rapid growth rate, fairly vigorous.

*Plant height.*—Five year old plants are about 2.5 to 5 meters.

*Plant width.*—Five year old plants are about 2 meters.

*Lateral branch description.*—Length: About 50 to 100 cm. Diameter: One year-old shoots, about 1 cm. Internode length: To about 10 cm. Color: Young: 144B. Woody: Slightly more brown than 197B. Texture: Rough; slightly grooved.

*Foliage description.*—Leaves simple, alternate; generally symmetrical. Quantity per lateral branch: About 15 to 25. Length, largest leaves: About 27 cm. Width, largest leaves: About 25 cm. Shape: Palmate, deeply lobed. Apex: Rounded. Base: Hastate to truncate. Margin: Entire, deeply lobed. Texture: Upper surface: Rough and pubescent. Lower surface: Velvety. Color: Young foliage, upper surface: 146A. Young foliage, lower surface: 146B. Fully expanded foliage, upper surface: 147A. Fully expanded foliage, lower surface: 146B. Venation, upper and lower surfaces: 143C. Petiole: Length: About 10 cm. Diameter: About 5 mm.

Flower description: Flowers minute, insignificant and typical of species.

*Natural flowering season.*—Summer to fall; consecutive flowering.

*Flower arrangement/type.*—Typically 15 to 25 flowers per lateral stem, one per leaf axil; older plants may have about 200 flowers. Not fragrant.

*Fruits.*—Time to fruiting: In Central Europe, initial fruit crop ripens at the end of July beginning of August; second fruit crop ripens in October Quantity: Typically 10 to 15 fruits are produced per lateral stem, almost one per every leaf axil; older plants may produce about 200 fruits per season. Number of days to fruit ripening: about 21. Keeping quality: About 2 to 3 days. Length: About 7 cm. Diameter: About 6 mm. Texture: Slight longitudinal grooves. Flavor: Very sweet; skin is sweet and not bitter. Color: Immature, 146A. Mature: 151A with overtones of 184B on upper surface.

Low temperature tolerance: Plants of the new Fig tree are tolerant to temperatures about −20° C.

Disease resistance: Plants of the new Fig tree have demonstrated good resistance to pathogens common to *Ficus carica.*

It is claimed:

1. A new and distinct cultivar of Fig tree named 'Violetta', as illustrated and described.

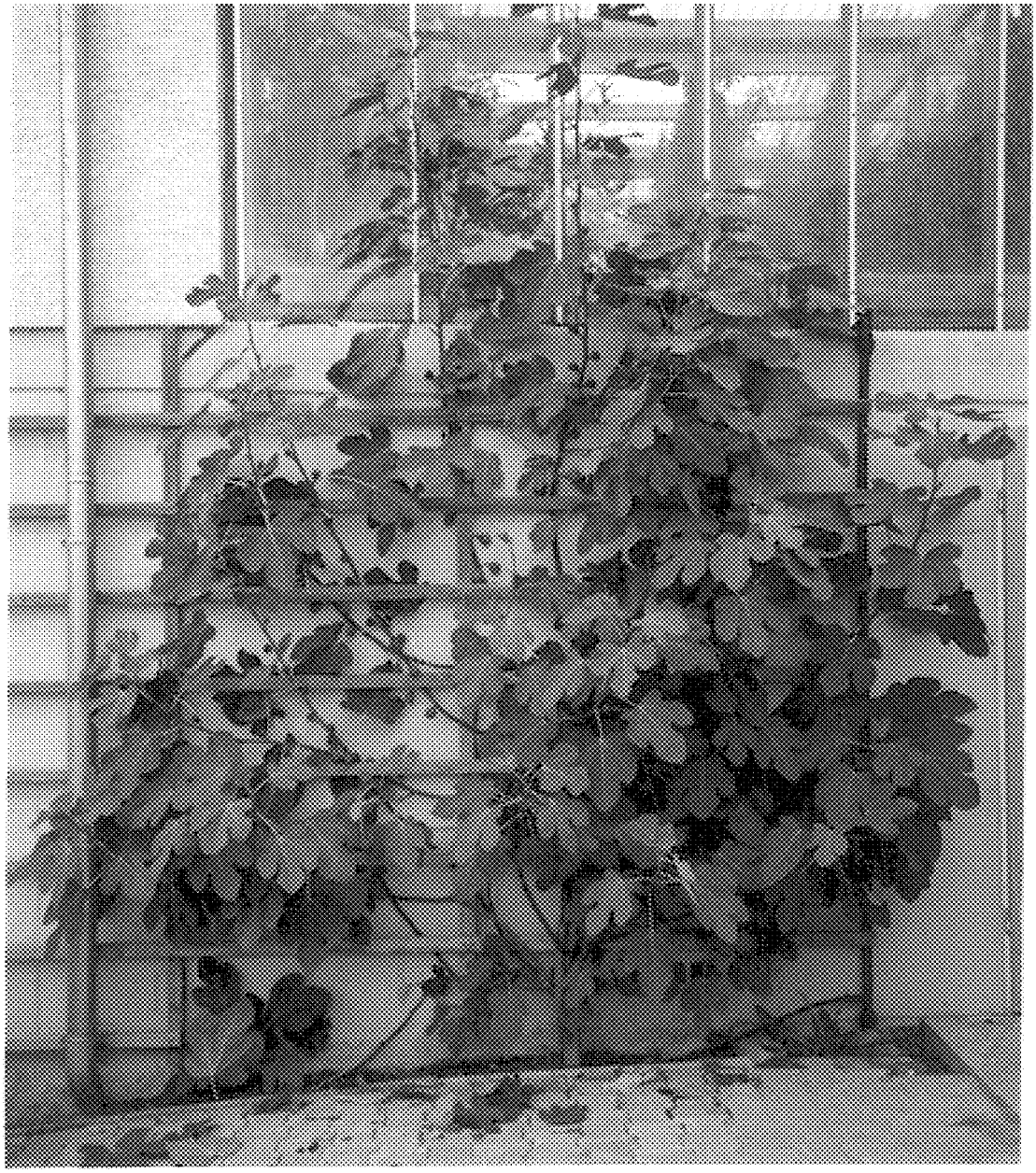

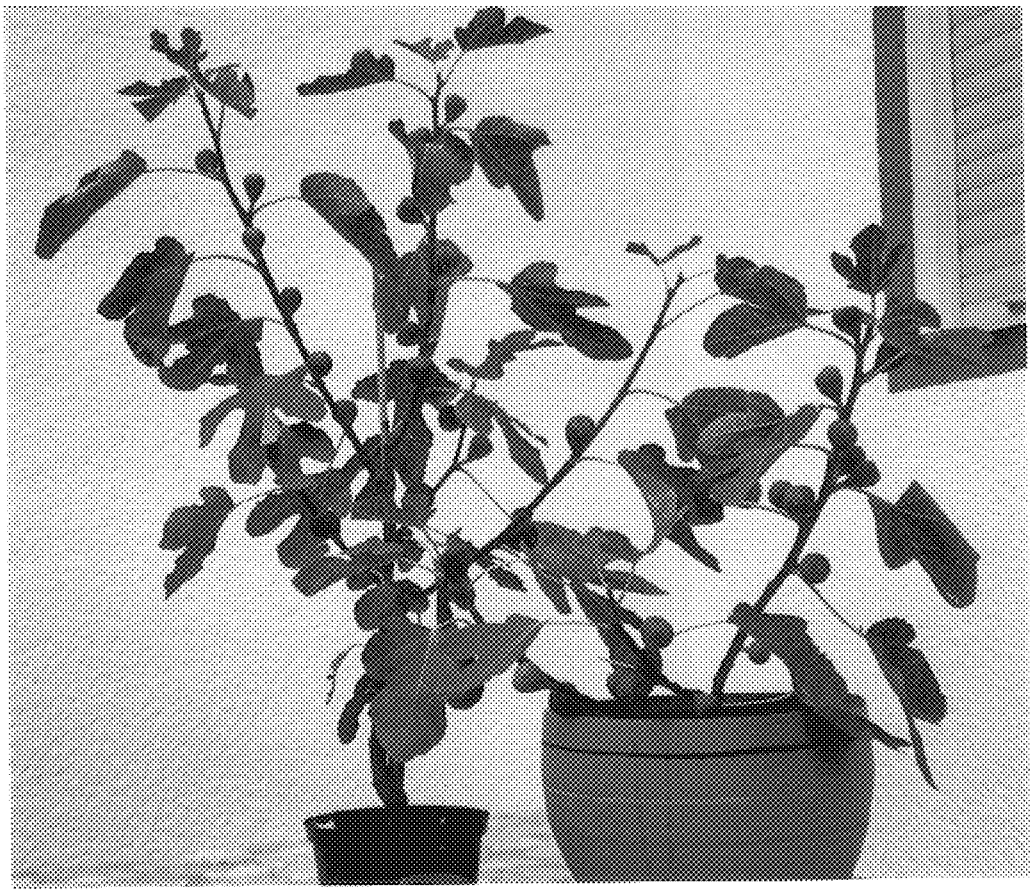

* * * * *